United States Patent
Muraki

(10) Patent No.: US 9,087,371 B2
(45) Date of Patent: Jul. 21, 2015

(54) MICROPARTICLE SORTING DEVICE AND METHOD OF OPTIMIZING FLUID STREAM THEREIN

(71) Applicant: Sony Corporation, Tokyo (JP)

(72) Inventor: Yosuke Muraki, Tokyo (JP)

(73) Assignee: Sony Corporation, Tokyo (JP)

( * ) Notice: Subject to any disclaimer, the term of this patent is extended or adjusted under 35 U.S.C. 154(b) by 59 days.

(21) Appl. No.: 14/118,788

(22) PCT Filed: Feb. 13, 2013

(86) PCT No.: PCT/JP2013/053324
§ 371 (c)(1),
(2) Date: Nov. 19, 2013

(87) PCT Pub. No.: WO2013/145905
PCT Pub. Date: Oct. 3, 2013

(65) Prior Publication Data
US 2014/0193059 A1    Jul. 10, 2014

(30) Foreign Application Priority Data
Mar. 30, 2012   (JP) ................ 2012-080609

(51) Int. Cl.
*G01N 15/14*    (2006.01)
*G06T 7/00*    (2006.01)

(52) U.S. Cl.
CPC .......... *G06T 7/0012* (2013.01); *G01N 15/1484* (2013.01); *G01N 2015/149* (2013.01); *G01N 2015/1415* (2013.01)

(58) Field of Classification Search
CPC .................... G01N 2015/149; G01N 15/1404; G01N 2015/1406; G01N 15/14; G01N 2015/1481; G01N 15/1463; G01N 2015/1415
See application file for complete search history.

(56) References Cited

U.S. PATENT DOCUMENTS

| | | | |
|---|---|---|---|
| 2004/0086159 A1 | 5/2004 | Lary et al. | |
| 2011/0033339 A1* | 2/2011 | Muraki | ................ 422/73 |
| 2013/0256136 A1 | 10/2013 | Muraki et al. | |
| 2013/0258075 A1 | 10/2013 | Muraki et al. | |
| 2014/0144817 A1 | 5/2014 | Hashimoto et al. | |
| 2014/0208875 A1 | 7/2014 | Muraki | |

FOREIGN PATENT DOCUMENTS

JP   2002-505423 A   2/2002
JP   2002-521658 A   7/2002

(Continued)

*Primary Examiner* — Amir Alavi
*Assistant Examiner* — Kenny Cese
(74) *Attorney, Agent, or Firm* — Wolf, Greenfield & Sacks, P.C.

(57) ABSTRACT

There is provided a microparticle sorting device that automatically optimizes a fluid stream.

There is provided a microparticle sorting device that includes a voltage supply unit that supplies a driving voltage to a vibratory element that applies vibration to an orifice that produces a fluid stream, a charge unit that imparts charge to at least some droplets ejected from the orifice, deflecting plates, arranged opposing each other with the fluid stream S therebetween, that vary a travel direction of the droplets, and a first image sensor that acquires an image of the droplets passing between the deflecting plates. The microparticle sorting device is equipped with a controller that detects the droplets in the image, sets a standard band corresponding to a width of the droplets before imparting the charge, and controls the driving voltage of the voltage supply unit so as to further decrease a quantity of the droplets detected in areas within a designated number of pixels from the standard band from among the droplets after imparting the charge.

20 Claims, 11 Drawing Sheets

(56) References Cited

FOREIGN PATENT DOCUMENTS

| | | |
|---|---|---|
| JP | 2009-145213 A | 7/2009 |
| JP | 2010-190680 A | 9/2010 |
| JP | 2010-216992 A | 9/2010 |
| JP | 2011-232033 A | 11/2011 |
| JP | 2011-237201 A | 11/2011 |
| WO | WO 01/02836 | 1/2001 |

* cited by examiner

FIG. 5
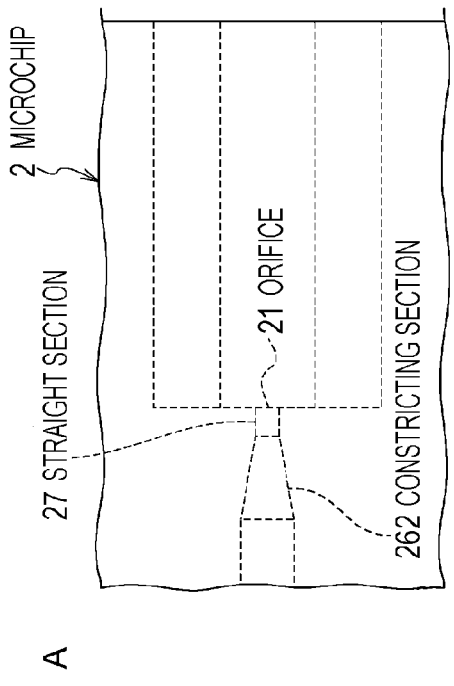
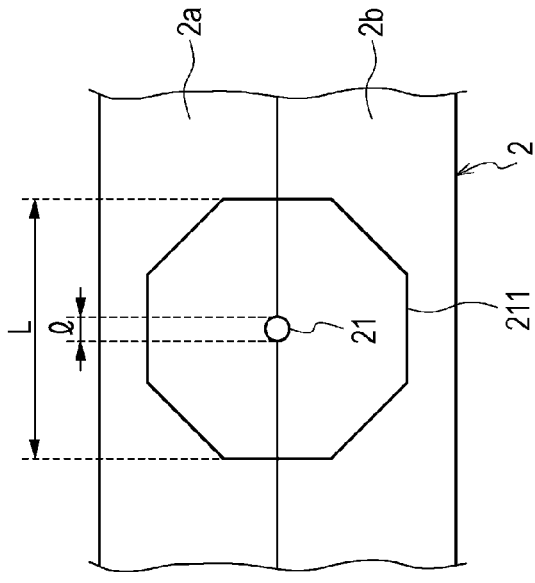
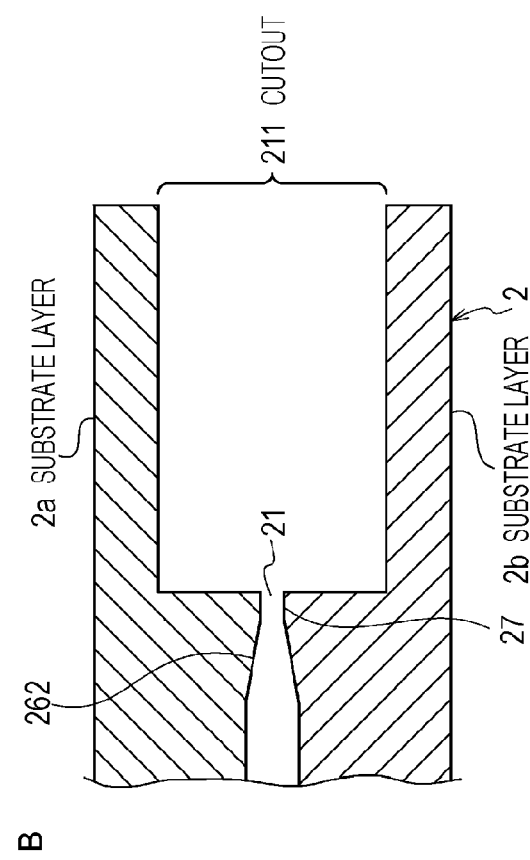

FIG. 7
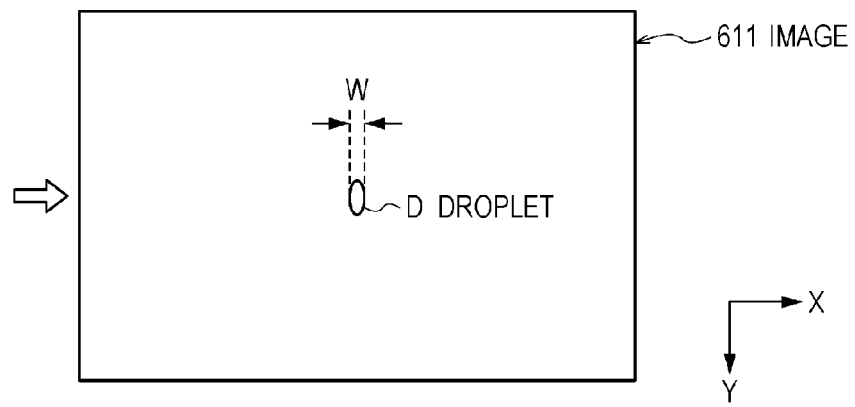
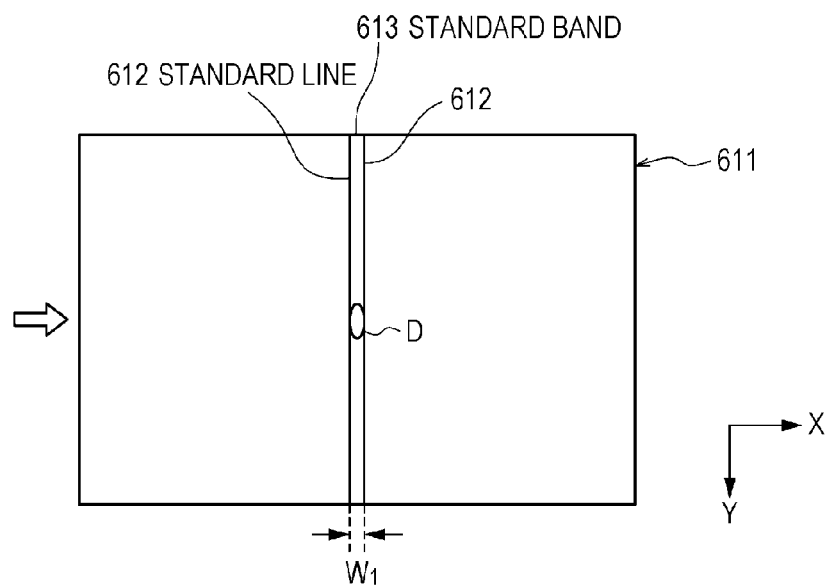

FIG. 8
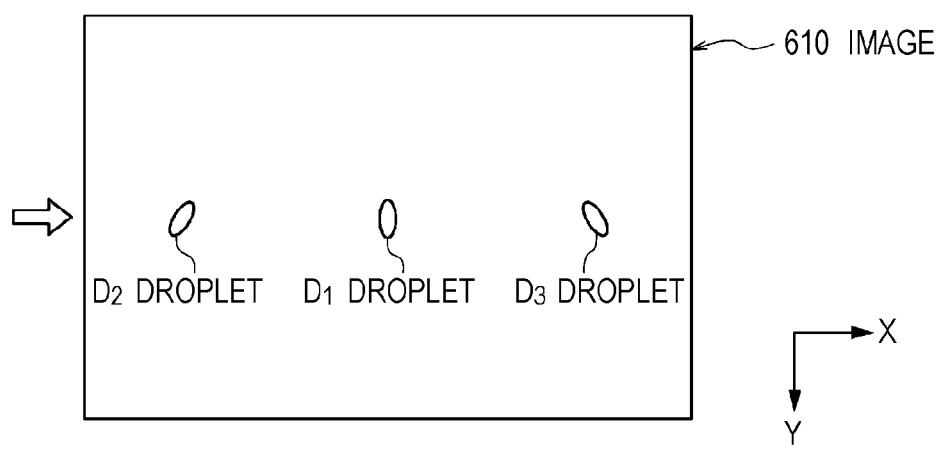
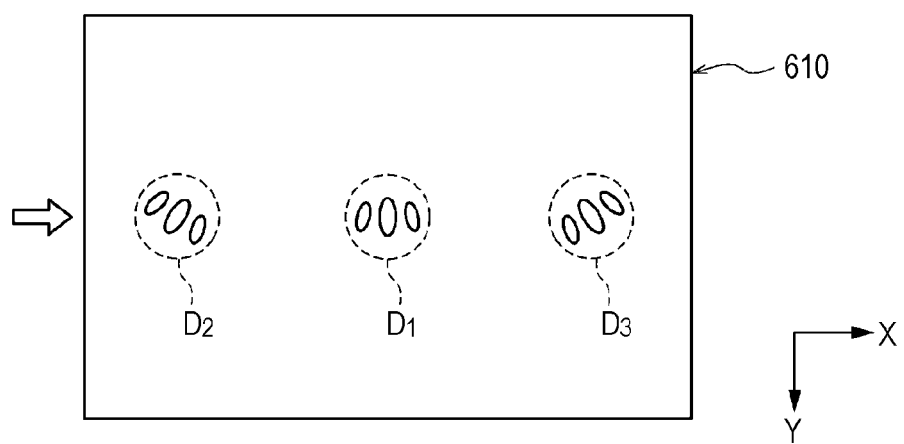

FIG. 9
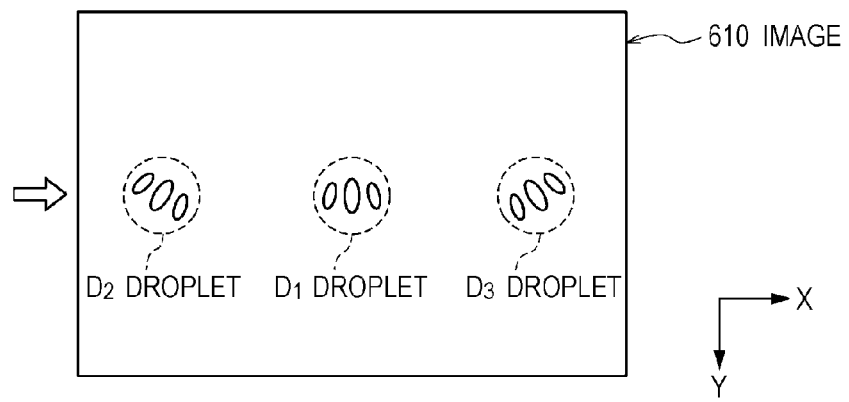
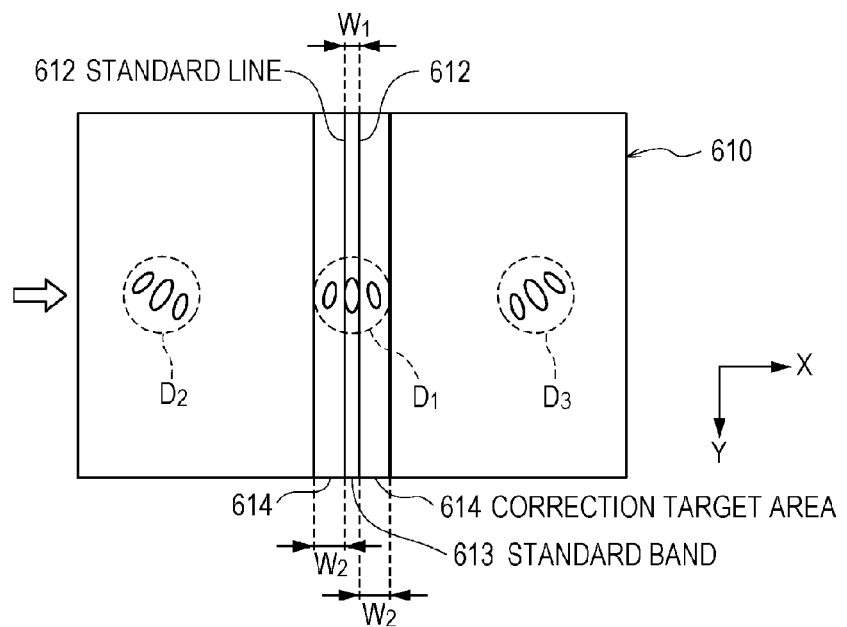

MICROPARTICLE SORTING DEVICE AND METHOD OF OPTIMIZING FLUID STREAM THEREIN

TECHNICAL FIELD

The present technology relates to a microparticle sorting device and a method of optimizing a fluid stream therein, and more specifically, to a microparticle sorting device and the like that automatically optimizes the state of a droplet ejected from an orifice.

BACKGROUND ART

There is known a microparticle sorting device (a flow cytometer, for example) that optically, electrically, or magnetically detects the properties of microparticles such as cells, and separates and collects only microparticles having a designated property.

Cell separation with a flow cytometer involves producing a fluid stream (a flow of droplets) by breaking a cell-containing sample liquid and a sheath liquid into droplets, which are ejected from an orifice formed on a flow cell or a microchip. The breaking of the sample liquid and the sheath liquid into droplets is performed by applying vibration at a designated frequency to the orifice with a vibratory element. The cell-containing droplets are imparted with an electric charge and ejected. By electrically controlling the direction of movement of each droplet, target cells having a desired property, and all other non-target cells, are collected in separate collecting receptacles.

For example, PTL 1 discloses, as a microchip-type flow cytometer, a "device for sorting particles provided with a microchip in which a flow channel through which liquid containing particles is flown and an orifice for discharging the liquid flowing through the flow channel to a space outside the chip are provided, a vibratory element for making and ejecting a droplet of the liquid at the orifice, a charging means for giving charge to the ejected droplet, an optical detecting means for detecting an optical characteristic of the particles flowing through the flow channel, paired electrodes arranged along the direction of movement of the ejected droplet and opposed with the moving droplet therebetween, and two or more vessels for collecting the droplet passing between the paired electrodes."

CITATION LIST

Patent Literature

PTL 1: Japanese Unexamined Patent Application Publication No. 2010-190680

SUMMARY OF INVENTION

Technical Problem

With a microparticle dispenser, in order to accurately perform electrical control of the direction of movement of a droplet, before analysis it is necessary to optimize the state of the fluid stream by adjusting factors such as the driving voltage and frequency of the vibratory element, as well as droplet charge timings. In the case where these adjustments are not performed appropriately, the fluid stream enters an unstable state, and cell sorting may become impossible, or the sorting precision may be lowered.

In the past, fluid stream optimization was performed by having a user adjust factors such as the driving voltage of the vibratory element while visually checking the state of the fluid stream, so as to produce a straight fluid stream with no instability. This operation required proficiency, and was problematic in terms of reliability and safety. Furthermore, the operation was extremely cumbersome, requiring optimization of the fluid stream to be performed every time the flow cell or microchip was replaced, or for every analysis.

Accordingly, the present technology takes as an object to provide a microparticle sorting device that automatically optimizes a fluid stream.

Solution to Problem

In order to solve the above problems, the present technology provides a microparticle sorting device that includes a voltage supply unit that supplies a driving voltage to a vibratory element that applies vibration to an orifice that produces a fluid stream, a charge unit that imparts charge to at least some droplets ejected from the orifice, deflecting plates, arranged opposing each other with the fluid stream therebetween, that vary a travel direction of the droplets, and a first image sensor that acquires an image of the droplets passing between the deflecting plates. The microparticle sorting device is equipped with a controller that detects the droplets in the image, sets a standard band corresponding to a width of the droplets before imparting the charge, and controls the driving voltage of the voltage supply unit so as to further decrease a quantity of the droplets detected in areas within a designated number of pixels from the standard band from among the droplets after imparting the charge. The controller detects the standard band in an image of the droplets before imparting the charge, and sets the standard band in an image of the droplets after imparting the charge. In the microparticle sorting device, by controlling the driving voltage of the voltage supply unit so as to further decrease a quantity of the droplets detected in areas within a designated number of pixels from the standard band, a driving voltage for a vibratory element that produces a stable fluid stream is automatically set.

The microparticle sorting device may also include a light source that irradiates the droplets passing between the deflecting plates with a laser. In this case, the controller is able to detect the droplets by image recognition of bright spots in the image. In addition, the controller may also control the driving voltage so as to further decrease a number of pixels in the bright spots detected in areas within a designated number of pixels from the standard band in an image of the droplets after imparting the charge. At this point, the controller may also control the driving voltage so as to minimize the number of pixels.

Also, the microparticle sorting device may also include a second image sensor that acquires an image of the droplets at a position where fluid exiting the orifice breaks into droplets. In this case, the controller is able to control the driving voltage such that a facing length along a travel direction of a droplet positioned between a microparticle-containing droplet immediately after dividing off from the fluid and the fluid becomes a designated length in the image.

The designated length is preferably 30% to 70% of a distance between the microparticle-containing droplet and the fluid.

In the microparticle sorting device, the first image sensor captures the droplets passing between the deflecting plates from a direction orthogonal to the fluid stream as well as a direction of opposition between the deflecting plates. Also, the deflecting plates vary a travel direction of the droplets with an electrical force acting on the charge imparted to the droplets.

The microparticle sorting device may be a microchip-type microparticle sorting device in which the orifice is formed on a replaceable microchip.

Also, the present technology provides a method of optimizing a fluid stream in a microparticle sorting device, including a first image acquiring step that acquires an image of droplets in a fluid stream produced from an orifice to which vibration is applied by a vibratory element, after passing between deflecting plates that vary a travel direction of the droplets, and a first voltage controlling step that detects the droplets in the image, sets a standard band corresponding to a width of the droplets before imparting charge, and sets the driving voltage of the vibratory element so as to further decrease a quantity of the droplets detected in areas within a designated number of pixels from the standard band from among the droplets after imparting charge. The first image acquiring step includes a step of acquiring an image of the droplets before imparting charge, and a step of acquiring an image of the droplets after imparting charge, and the first voltage controlling step includes a step of detecting the standard band in the image of the droplets before imparting charge, and a step of setting the standard band in the image of the droplets after imparting charge.

In the method of optimizing a fluid stream, in the case where the droplets passing between the deflecting plates are irradiated with a laser in the first image acquiring step, the droplets may be detected by image recognition of bright spots in the image in the first voltage controlling step. In addition, in the first voltage controlling step, the driving voltage may also be controlled so as to further decrease a number of pixels in the bright spots detected in areas within a designated number of pixels from the standard band in an image of the droplets after imparting the charge. At this point, the controller may also control the driving voltage so as to minimize the number of pixels.

Also, the method of optimizing a fluid stream may also include a second image acquiring step that acquires an image of the droplets at a position where fluid exiting the orifice breaks into droplets, and a second voltage controlling step that sets the driving voltage such that a facing length along a travel direction of a droplet positioned between a microparticle-containing droplet immediately after dividing off from the fluid and the fluid becomes a designated length in the image.

In this case, the designated length may be 30% to 70% of a distance between the microparticle-containing droplet and the fluid.

In the method of optimizing a fluid stream, preferably the second image acquiring means and the second voltage controlling step are performed after the first image acquiring means and the first voltage controlling step, the driving voltage is adjusted roughly in the first voltage controlling step, and the driving voltage is adjusted finely in the second voltage controlling step.

In the method of optimizing a fluid stream, in the first image acquiring step, the droplets passing between the deflecting plates are captured from a direction orthogonal to the fluid stream as well as a direction of opposition between the deflecting plates.

In the present technology, a "microparticle" is taken to broadly include biological microparticles such as cells, microorganisms, and liposomes, synthetic particles such as latex particles, gel particles, and industrial particles, or the like.

Biological microparticles include chromosomes, liposomes, mitochondria, organelles (organelle) and the like constituting various cells. Cells include animal cells (such as hemocyte-related cells) as well as plant cells. Microorganisms include bacteria such as *E. coli*, viruses such as tobacco mosaic virus, and fungi such as yeast. Furthermore, biological microparticles are also taken to potentially encompass biological macromolecules such as nucleic acids, proteins, and complexes thereof. Meanwhile, industrial particles may be organic or inorganic polymer materials, metals, or the like, for example. Organic polymer materials include polystyrene, styrene-divinylbenzene, poly(methyl methacrylate), and the like. Inorganic polymer materials include glass, silica, magnetic materials, and the like. Metals include metal colloids, aluminum, and the like. Although it is normal for the shapes of these microparticles to be spherical generally, the shapes may also be non-spherical, and factors such as size and mass are not particularly limited.

Advantageous Effects of Invention

According to the present technology, there is provided a microparticle sorting device that automatically optimizes a fluid stream.

BRIEF DESCRIPTION OF DRAWINGS

FIG. 5 is a diagram for explaining a configuration of an orifice 21 of the microchip 2.

FIG. 7 is a diagram for explaining an image process in an image acquiring/standard line setting step $S_2$.

FIG. 8 is a diagram for explaining an image acquired in an image acquiring/pixel information acquiring step $S_5$.

FIG. 9 is a diagram for explaining an image process in an image acquiring/pixel information acquiring step $S_5$.

DESCRIPTION OF EMBODIMENT

Hereinafter, a preferred embodiment for carrying out the present technology will be described with reference to the drawings. Note that the embodiment described hereinafter is one that illustrates an example of a representative embodiment of the present technology, and the scope of the present technology should not be narrowly interpreted thereby. The description will proceed in the following order.

Figure 1:
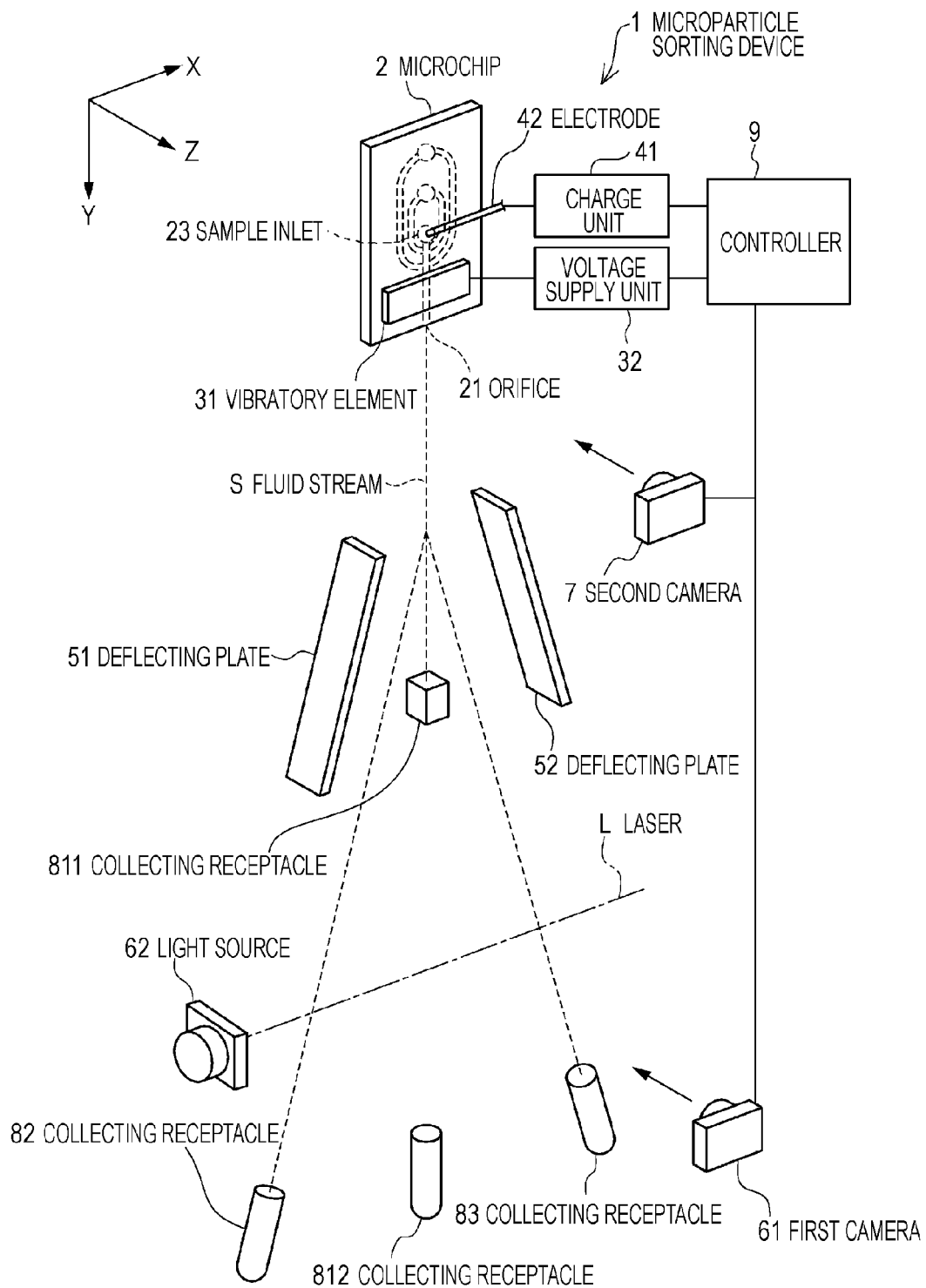
FIG. 1 is a diagram for explaining a sorting-related configuration of a microparticle sorting device 1 (flow cytometer 1) according to the present technology, configured as a microchip-type flow cytometer.
Figure 2:
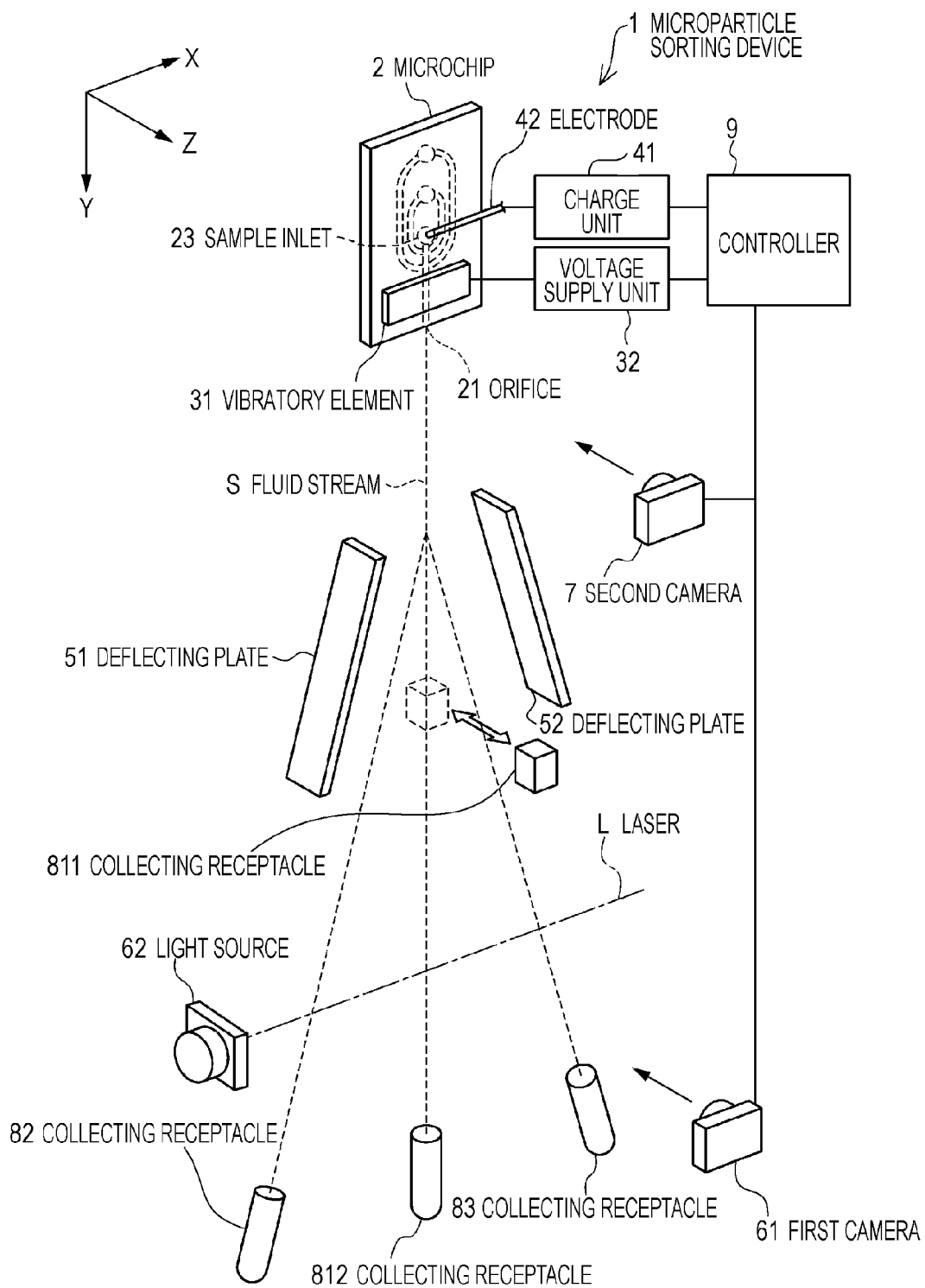
FIG. 2 is a diagram for explaining a sorting-related configuration of the flow cytometer 1.

1. Configuration of microparticle sorting device according to present technology
(1-1) Voltage supply unit
(1-2) Charge unit
(1-3) Deflecting plates
(1-4) Collecting receptacles
(1-5) First image sensor and second image sensor
(1-6) Controller and the like
(1-7) Microchip
2. First procedure for optimization control of fluid stream in microparticle sorting device according to present technology
(2-1) Collecting receptacle retracting step $S_1$
(2-2) Image acquiring/standard band setting step $S_2$
(2-3) Charge voltage applying step $S_3$
(2-4) Drive value adjusting step $S_4$
(2-5) Image acquiring/pixel information acquiring step $S_5$
(2-6) Optimal drive value searching step $S_6$
(2-7) Drive value setting step $S_7$
(2-8) Collecting receptacle returning step $S_8$
3. Second procedure for optimization control of fluid stream in microparticle sorting device according to present technology
(3-1) Charge voltage applying step $S_{13}$
(3-2) Drive value adjusting step $S_{14}$
(3-3) Image acquiring/satellite information acquiring step $S_{15}$
(3-4) Optimal drive value searching step $S_{16}$
(3-5) Drive value setting step $S_{17}$ 1. Configuration of Microparticle Sorting Device According to Present Technology FIGS. 1 and 2 are schematic diagrams explaining a sorting-related configuration of a microparticle sorting device 1 (hereinafter also designated the "flow cytometer 1") according to the present technology, configured as a microchip-type flow cytometer.

(1-1) Voltage Supply Unit

The flow cytometer 1 is equipped with a vibratory element 31 that applies vibration to an orifice 21 formed on a microchip 2, causing a laminar flow of a cell-containing sample liquid and a sheath liquid exiting from the orifice 21 to break into droplets and be ejected. The vibratory element 31 may be a piezo element, for example. The ejected droplets become a fluid stream S and are projected in the positive Y-axis direction of the drawing. Note that the microchip 2 is replaceably mounted in the flow cytometer 1.

Also, the flow cytometer 1 is equipped with a voltage supply unit 32 that supplies a driving voltage to the vibratory element 31. In the flow cytometer 1, the vibratory element 31 may be integrated with the microchip 2, or disposed on the device side so as to enable contact with a mounted microchip 2. In the case of disposing the vibratory element 31 on the microchip 2 side, a connector that connects the vibratory element 31 and the voltage supply unit 32 is provided in the flow cytometer 1.

(1-2) Charge Unit

Droplets ejected from the orifice 21 are imparted with a positive or negative charge by the charge unit 41. The charging of droplets is performed by an electrode 42 electrically connected to the charge unit 41, and inserted into a sample inlet 23 provided on the microchip 2. Note that the electrode 42 is assumed to be one that may be inserted at any location on the microchip 2 to make electrical contact with a sample liquid or sheath liquid sent through a flow channel.

Figure 3:
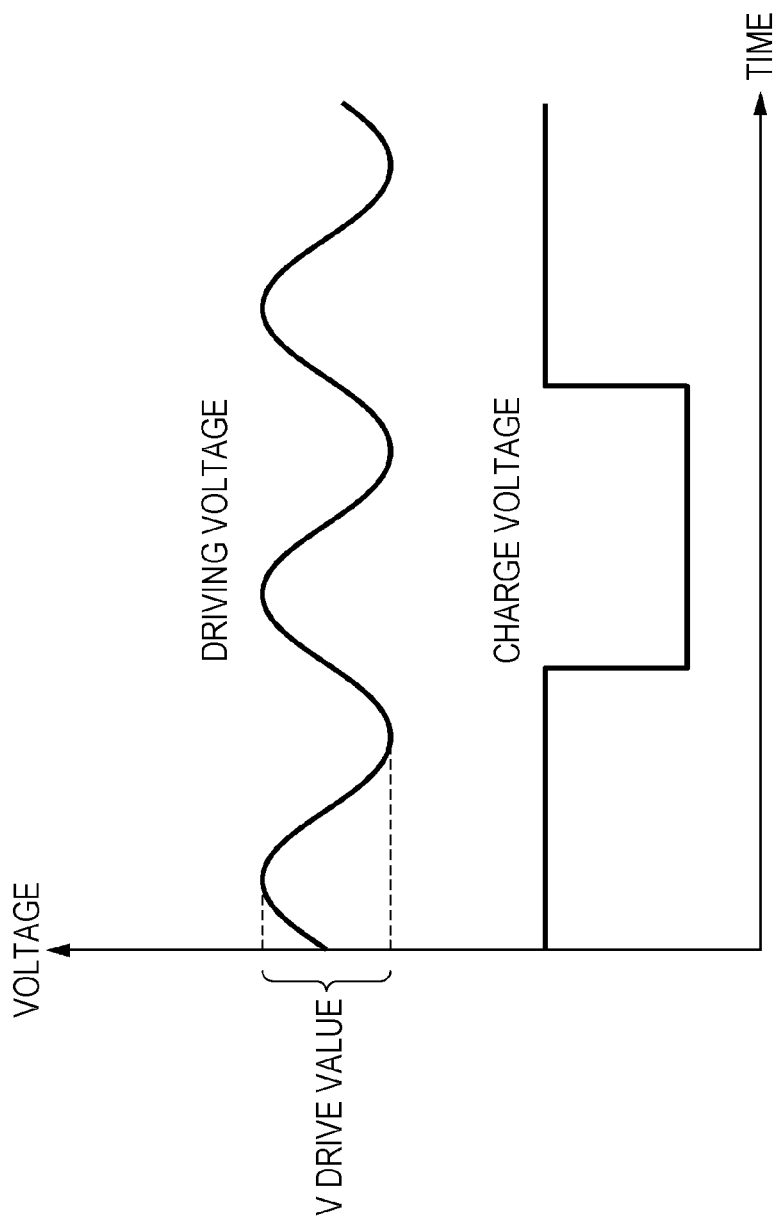
FIG. 3 is a diagram for explaining an example of a synchronization pattern between the frequency of the driving voltage of a vibratory element 31, and the voltage charge timings of a charge unit 41.

In the flow cytometer 1, by synchronizing the frequency of the driving voltage of the vibratory element 31 with the switching timings of the voltage of the charge unit 41 (the charge voltage), some of the droplets ejected from the orifice 21 are imparted with a positive or a negative charge. Some of the droplets may also be uncharged, without being imparted with a charge. FIG. 3 illustrates an example of a synchronization pattern between the frequency of the driving voltage of the vibratory element 31, and the voltage charge timings of the charge unit 41. The sign V in the drawing indicates the driving voltage (drive value) of the vibratory element 31.

(1-3) Deflecting Plates

Furthermore, the flow cytometer 1 is equipped with a pair of deflecting plates 51 and 52 arranged to oppose each other with the fluid stream S therebetween (see FIGS. 1 and 2). The deflecting plates 51 and 52 may be ordinarily-used electrodes. In the drawing, the direction of opposition between the deflecting plates 51 and 52 is indicated by the X-axis direction.

(1-4) Collecting Receptacles

A fluid stream passing between the deflecting plates 51 and 52 is received into any of a collecting receptacle 811, a collecting receptacle 82, or a collecting receptacle 83. For example, in the case where the deflecting plate 51 is positively charged and the deflecting plate 52 is negatively charged, droplets that have been negatively charged by the charge unit 41 are collected by the collecting receptacle 82, whereas positively charged droplets are collected by the collecting receptacle 83. Meanwhile, droplets not charged by the charge unit 41 fly straight without being subjected to an electrical acting force from the deflecting plates 51 and 52, and are collected by the collecting receptacle 811. In the flow cytometer 1, by controlling the travel direction of a droplet according the properties of cells contained in each liquid, it is possible to collect target cells have a desired property, and all other non-target cells, in separate collecting receptacles.

In the flow cytometer 1, the collecting receptacle 811 is configured to be retractable from between the deflecting plates 51 and 52 (see the block arrow in FIG. 2). At the initial position illustrated in FIG. 1, the collecting receptacle 811 receives uncharged droplets flying straight in the positive Y-axis direction. In contrast, at the retracted position of the collecting receptacle 811 illustrated in FIG. 2, uncharged droplets flying straight are received into a collecting receptacle 812 arranged below the collecting receptacle 811. The collecting receptacle 812 together with the collecting receptacles 82 and 83 are disposed in a line in the direction of opposition between the deflecting plates 51 and 52 (X-axis direction). Note that although the drawings illustrate the case where the retracted position of the collecting receptacle 811 is set to a position a designated distance away from the initial position in the positive Z-axis direction, the retracted position of the collecting receptacle 811 is arbitrary, insofar as uncharged droplets flying straight in the positive Y-axis direction are able to reach the collecting receptacle 812.

The collecting receptacles 811, 812, 82, and 83 may be general-purpose plastic tubes or glass tubes for experimental use. It is preferable for these collecting receptacles to be replaceably arranged in the flow cytometer 1. Also, from among the collecting receptacles, the ones that receive non-target cells may also connect to a drainage channel for collected droplets. Note that the number of collecting receptacles arranged in the flow cytometer 1 is not taken to be particularly limited. In the case of arranging more than three collecting receptacles, each droplet is guided to and collected by one of the collecting receptacles, according to the presence or absence of an electrical acting force between the deflecting plates 51 and 52, and its size.

(1-5) First Image Sensor and Second Image Sensor

The sign 61 in the drawings indicates a first image sensor (camera) that captures an image of a droplet passing through between the deflecting plates 51 and 52 from a direction orthogonal to the fluid stream S and the direction of opposition between the deflecting plates 51 and 52 (the Z-axis direction). The light source 62 illuminates the imaging area by the first camera 61. The first camera 61 may be imaging means such as a CCD camera, a line sensor, a single-layer photodiode, or other such photoelectric transducer. Also, an LED as well as an LD or other laser light source, a xenon light, an incandescent bulb or the like may be used for the light source 62.

Also, the sign 7 in the drawings indicates a second image sensor (camera) that captures an image of a droplet at the position where the laminar flow of sample liquid and sheath liquid exiting the orifice 12 breaks into droplets (the break-off point). The second camera 7 may be a CCD camera or the like, similarly to the first camera 61. In order to capture an image of a droplet with the second camera 7, a light source (strobe), not illustrated, that illuminates the imaging area similarly to the light source 62 may also be provided.

The first camera 61 and the second camera 7, together with the controller described next, function in order to optimize the fluid stream S to reach a straight state with no instability. Control steps for optimizing the fluid stream S will be discussed later.

(1-6) Controller and the Like

In addition to the configuration discussed above, the flow cytometer 1 is also provided with structural elements provided in an ordinary flow cytometer, such as a light-radiating detector for detecting the optical properties of cells, a data analyzer for determining properties, and a tank unit that stores sample liquid and sheath liquid, as well a controller 9 for controlling these respective structural elements.

The controller 9 may be realized by a general-purpose computer equipped with a CPU, memory, and a hard disk or the like. The hard disk stores information such as an OS and a program that executes the control steps described next.

Also, the light-radiating detector is realized by a laser light source, a radiating subsystem made up of a condenser lens that condenses and radiates the laser onto cells as well as a dichroic mirror, a band-pass filter, and the like, and a detecting subsystem that detects measuring target light produced from cells due to laser radiation. The detecting subsystem is realized by a photo multiplier tube (PMT), an area image sensor such as a CCD or CMOS sensor, or the like, for example.

Measuring target light detected by the detecting subsystem of the light-radiating detector is light produced from cells due to the radiation of measuring light, and may be forward-scattered light or back-scattered light, scattered light such Rayleigh scattering or Mie scattering, fluorescence, or the like, for example. The measuring target light is converted into an electrical signal, output to the controller 9, and submitted to determine the optical properties of cells.

Note that the flow cytometer 1 may also be taken to be one that magnetically or electrically detects cell properties. In this case, microelectrodes are disposed opposing each other in the sample flow channel 22 of the microchip 2 described next, and information such as the resistance value, capacitance value (capacitance value), inductance value, impedance, a value of change in the electric field between the electrodes, or the magnetization, magnetic field change, and magnetic field is measured.

(1-7) Microchip

Figure 4:
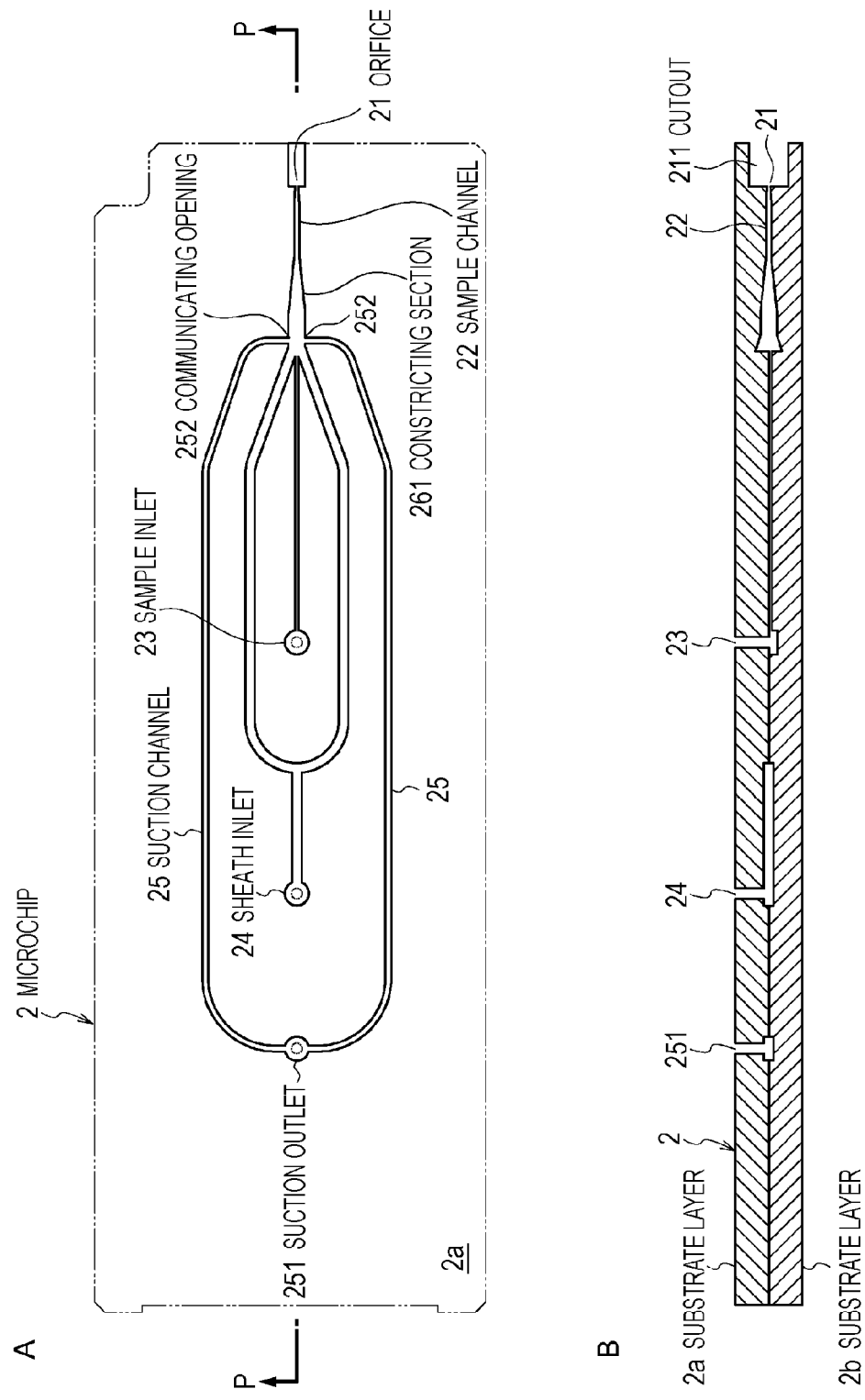
FIG. 4 is a diagram for explaining a configuration of an exemplary microchip 2 mountable in the flow cytometer 1.

FIGS. 4 and 5 illustrate an example of a microchip 2 mountable in the flow cytometer 1. FIG. 4A is a schematic top view, while B illustrates a schematic cross-section view corresponding to the cross-section P-P in A. Meanwhile, FIG. 5 is a diagram that schematically explains a configuration of the orifice 21 of the microchip 2, with A being a top view, B being a cross-section view, and C being a front view. FIG. 5B corresponds to the P-P cross-section in FIG. 4A.

The microchip 2 is made by aligning together substrate layers 2a and 2b in which a sample channel 22 is formed. The formation of the sample channel 22 in the substrate layers 2a and 2b may be performed by injection molding of a thermoplastic resin using a metal mold. Plastics that have been established as materials for microchips in the past, such as polycarbonate, poly(methyl methacrylate) (PMMA), cyclic polyolefin, polyethylene, polystyrene, polypropylene, and polydimethylsiloxane (PDMS) may be adopted for the thermoplastic resin.

Sample liquid is introduced into a sample inlet 23, converges with sheath liquid introduced into a sheath inlet 24, and is sent through a sample channel 22. Sheath liquid introduced from the sheath inlet 24, after being divided and sent in two direction, converges with the sample liquid so as to enclose the sample liquid from two directions in a convergence section with the sample liquid introduced from the sample inlet 23. Thus, a 3D laminar flow is formed in the convergence section, with a sample liquid laminar flow positioned in the center of a sheath liquid laminar flow.

The sign 25 indicates a suction channel used when blockage or air bubbles occur in the sample channel 22, and is for eliminating blockage or air bubbles by applying negative pressure inside the sample channel 22 and temporarily reversing the flow. At one end of the suction channel 25, there is formed a suction outlet 251 connected to a negative pressure source such as a vacuum pump, while the other end connects to the sample channel 22 at a communicating opening 252.

The laminar flow width of the 3D laminar flow is constricted in constricting sections 261 (see FIG. 4) and 262 (see FIG. 5), which are formed such that the surface area of a vertical cross-section with respect to the sending direction becomes smaller in a gradual or stepwise manner from upstream to downstream in the sending direction. After that, the 3D laminar flow exits the orifice 21 provided on one end of the flow channel.

The detection of cell properties is performed between the constricting section 261 and the constricting section 262 of the sample channel 22. With optical detection, for example, cells sent in a line at the center of the 3D laminar flow in the sample channel 22 are irradiated with a laser by a light-radiating detector not illustrated, and scattered light or fluorescent light produced from the cells is detected by a photodetector.

The connecting section to the orifice 21 of the sample channel 22 is made to be a linearly-formed straight section 27. The straight section 27 functions to project the fluid stream S from the orifice 21 straight in the positive Y-axis direction.

The 3D laminar flow exiting the orifice 21 breaks into droplets due to vibration applied to the orifice 21 by the vibratory element 31, and is projected as a fluid stream S (see FIG. 1). The orifice 21 has an opening in the direction of the edge face of the substrate layers 2a and 2b, and a cutout 211 is provided between the position of the opening and the substrate layer edge face. The cutout 211 is formed by cutting out the substrate layers 2a and 2b between the position of the opening of the orifice 21 and the substrate layer edge face, such that the diameter L of the cutout 221 becomes greater than the opening diameter 1 of the orifice 21 (see FIG. 5C). It is desirable to make the diameter L of the cutout 211 at least twice as large as the opening diameter 1 of the orifice 21, so as to not obstruct the movement of droplets ejected from the orifice 21.

Figure 6:
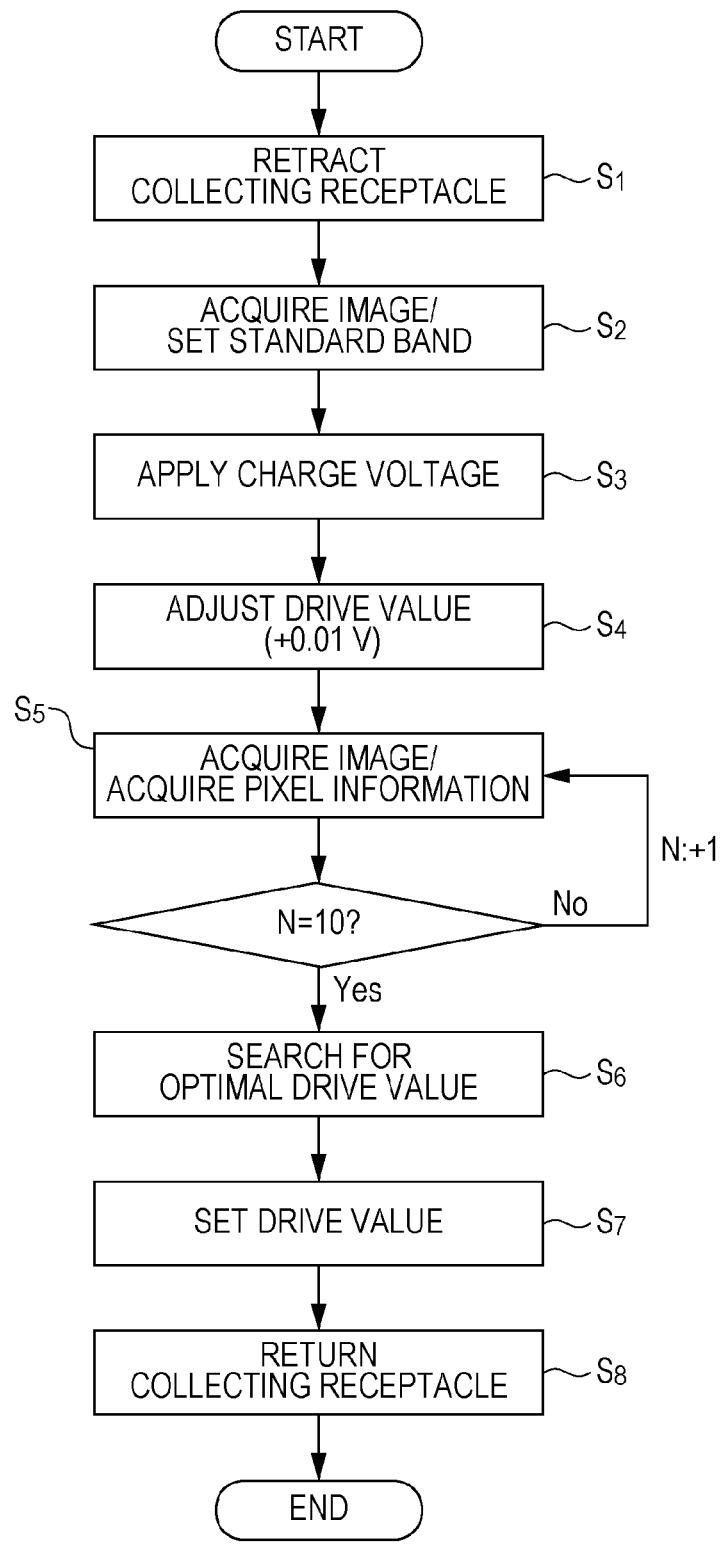
FIG. 6 is a flowchart for explaining control steps for optimizing a fluid stream S in the flow cytometer 1.

2. First Procedure for Optimization Control of Fluid Stream in Microparticle Sorting Device According to Present Technology FIG. 6 is a flowchart for explaining a first procedure of control steps for optimizing a fluid stream S in the flow cytometer 1. The control steps include a "collecting receptacle retracting step $S_1$", an "image acquiring/standard band setting step $S_2$", a "charge voltage applying step $S_3$", a "drive value adjusting step $S_4$", an "image acquiring/pixel information acquiring step $S_5$", an "optimal drive value searching step $S_6$", a "drive value setting step $S_7$", and a "collecting receptacle returning step $S_8$". Each step is described below.

(2-1) Collecting Receptacle Retracting Step $S_1$

If an analysis start signal is input by a user, the controller 9 drives the pumps of tanks storing sample liquid and sheath liquid, and starts sending sample liquid and sheath liquid to the sample inlet 23 and the sheath inlet 24 of the microchip 2. Furthermore, the controller 9 starts the application of vibration to the orifice 21 by the vibratory element 31. Thus, a 3D laminar flow of sample liquid and sheath liquid projected from the orifice 21 is broken into droplets and ejected to produce a fluid stream S. At this point, the voltage supplied to the vibratory element 31 by the voltage supply unit 32 is taken to be an initial value $V_0$. The initial value $V_0$ is a value set according to the opening diameter 1 of the orifice 21 (see FIG. 5) and the frequency of the vibratory element 31.

The fluid stream S is projected straight out from the orifice 21, and collected in the collecting receptacle 811 (see FIG. 1). Droplets collected and stored inside the collecting receptacle 811 preferably exit the receptacle from a drainage channel connected to the collecting receptacle 811.

The control steps for optimizing the fluid stream S start with a step $S_1$, in which the collecting receptacle 811 receiving the fluid stream S projected from the orifice 21 is retracted out from between the deflecting plates 51 and 52. Retracting the collecting receptacle 811 causes the fluid stream S to reach the collecting receptacle 812 arranged below the collecting receptacle 811, and causes the fluid stream S to pass through the imaging area of the first camera 61 and the illumination area of the light source 62, and be collected in the collecting receptacle 812. For the retracted position of the collecting receptacle 811, see FIG. 2.

(2-2) Image Acquiring/Standard Band Setting Step $S_2$

In this step $S_2$, the first camera 61, having received a signal from the controller 9, acquires an image of a droplet in the fluid stream S. FIG. 7A illustrates an example of an acquired image. In the image 611, droplets D at a position irradiated by a laser L from the light source 62 (see the block arrow in the drawing) are detected as high-brightness pixels (a bright spot).

Furthermore, in this step $S_2$, the droplets D are detected by image recognition of the bright spot, two standard lines 612 and 612 corresponding to the width w of the droplets D are set, and the area between the standard lines 612 and 612 is set as a standard band 613 (see FIG. 7B). The image 611 used for image recognition is preferably an accumulation of images acquired for two or more (preferably many) droplets.

The standard lines 612 and 612 are set parallel to the direction of projection of the fluid stream S (the positive Y-axis direction). Also, the distance between the standard lines 612 and 612 (the width of the standard band 613) $W_1$ is set equal to the width w of the droplets D, or slightly larger than the width w. Suitable set values for the width $W_1$ of the standard band 613 will be further discussed later.

Position information about the standard lines 612 and 612 as well as the standard band 613 in the image 611 is stored by the controller 9, and utilized in a later step $S_5$.

(2-3) Charge Voltage Applying Step $S_3$

In this step $S_3$, the charge unit 41, having received a signal from the controller 9, starts charging droplets. Thus, droplets having a positive charge, droplets having no charge, and droplets having a negative charge come to be contained in the fluid stream S. Respective droplets are subjected to an electrical force acting between the deflecting plates 51 and 52, and travel in a direction according to their charge (see FIG. 2).

(2-4) Drive Value Adjusting Step $S_4$

In this step $S_4$, the controller 9 outputs a signal to the voltage supply unit 32, causing the driving voltage of the vibratory element 31 to increase or decrease from the initial value $V_0$ by a fixed increment. The increment of increase and the increment of decrease may be set as appropriate. Herein, the case of increasing by 0.01 V will be described as an example.

(2-5) Image Acquiring/Pixel Information Acquiring Step $S_5$

If the drive value of the vibratory element 31 is set to $(V_0+0.01)$ V, the controller 9 outputs a signal to the first camera 61, and the first camera 61 acquires an image of droplets in the fluid stream S. FIG. 8 illustrates an example of an acquired image. In the image 610, droplets at positions irradiated by a laser L from the light source 62 (see the block arrow in the drawing) are detected as bright spots. In the image 610, uncharged droplets $D_0$ falling straight into the collecting receptacle 812 (see FIG. 2), negatively charged droplets $D_2$ falling diagonally towards the collecting receptacle 82, and positively charged droplets $D_3$ falling diagonally towards the collecting receptacle 83 are detected as bright spots (see FIG. 8A). Hereinafter, a fluid stream formed by straight-falling droplets $D_1$ will be designated the "main stream", whereas fluid streams formed by diagonally-falling droplets $D_2$ or droplets $D_3$ will be designated "side streams".

The image 610 is taken to be an accumulation of images acquired for two or more (preferably many) droplets. In this case, in the case where the initial value $V_0$ for the drive value of the vibratory element 31 is not an optimal value, the droplets $D_1$, $D_2$, and $D_3$ are not respectively detected as single bright spots as illustrated in FIG. 8A, but instead are respectively detected as multiple, divided bright spots as illustrated in FIG. 8B. This is because the fluid stream S is in an unstable state, and thus inconsistencies occur in the positions of the droplets $D_1$, $D_2$, and $D_3$ among the respective images constituting the accumulated image. Inconsistencies in the position of the droplets $D_1$ occur because some of the droplets $D_1$ constituting the main stream are imparted with a slight charge. Likewise, inconsistencies in the positions of the droplets $D_2$ and $D_3$ also happen because of inconsistent charges occurring among the droplets $D_2$ or the droplets $D_3$ constituting a side stream. With the fluid stream S in an unstable state, fine control of the travel direction is not possible, and the droplets $D_1$, $D_2$, and $D_3$ cannot be sorted into the respective collecting receptacles 812, 82, and 83, or the sorting precision is lowered.

In this step $S_5$ and the subsequent optimal drive value searching step $S_6$, a search is performed to find a drive value V such that the fluid stream S will reach an optimal state with no instability. First, in this step $S_5$, the controller 9 sets the standard lines 612 and 612 as well as the standard band 613 in the image 610, on the basis of the position information for the standard lines 612 and 612 as well as the standard band 613 that were set in the image 611 in the above step $S_2$ (see FIG. 9B). Then, the number of pixels (pixel information) in bright spots detected in areas within a designated number of pixels from the standard band 613 (in the drawing, correction target areas 614) is computed.

The standard band 613 is the area in which a bright spot due to droplets D before charging were detected in the image 611 acquired in the above step $S_2$, and is the area in which a bright spot was detected in the image 610 as a result of uncharged droplets falling straight into the collecting receptacle 812 (see FIG. 2) from among the droplets $D_1$ forming the main stream.

On the other hand, the correction target areas 614 in the image 610 are the areas in which bright spots were detected as a result of the droplets imparted with a slight charge from among the droplets $D_1$ forming the main stream, thereby causing inconsistencies.

The width $W_1$ of the standard band 613 is preferably the same as the width w of the droplets D (see FIG. 7), but may also be set larger than the width w as long as bright spots due to droplets causing inconsistencies within the standard band 613 are not detected. Also, the widths $W_2$ of the correction target areas 614 may be set as a suitable number of pixels from a standard line 612. However, if the widths $W_2$ are too large, bright spots due to the droplets $D_2$ and $D_3$ constituting the side streams will be detected within the correction target areas 614, which is not preferable.

This step $S_5$ is repeatedly executed multiple times, in which the acquisition of an image 610 and the computation/storage of the number of pixels (pixel information) in bright spots detected within the correction target areas 614 in the image 610 are performed for different values of the drive value V of the vibratory element 31. For example, in the case of increasing the drive value V of the vibratory element 31 by 0.01 V, at first image acquisition and pixel count computation are performed after setting the drive value to $(V_0+0.01)$ V. Subsequently, image acquisition and pixel count computation are performed up to an Nth time while taking the drive value to be $(V_0+0.01 \times N)$ V. The number of repetitions N may be set as appropriate, and may be approximately 10 times, for example.

(2-6) Optimal Drive Value Searching Step $S_6$

After repeating the image acquiring/pixel information acquiring step $S_5$ a prescribed number of times, the controller 9 determines an optimal drive value $V_s$ that will further reduce, and preferably minimize, the number of pixels in bright spots detected within the correction target areas 614. Specifically, the number of pixels (pixel information) in bright spots detected within the correction target areas 614 is compared among the respective images 610 acquired in the image acquiring/pixel information acquiring step $S_5$ from the 1st to Nth times. Then, the repetition with the minimum number of pixels is identified, and the drive value V for that case is obtained as the optimal drive value $V_s$.

Further reducing the number of pixels in bright spots detected within the correction target areas 614 is substantially equivalent to further increasing the number of pixels in the bright spot detected within the standard band 613. Bright spots detected within the correction target areas 614 are due to droplets imparted with a slight charge from among the droplets $D_1$ forming the main stream, thereby causing inconsistencies. Meanwhile, the bright spot detected within the standard band 613 is due to uncharged droplets falling straight into the collecting receptacle 812 (see FIG. 2) from among the droplets $D_1$ forming the main stream. Consequently, minimizing the detected number of pixels in bright spots detected within the correction target areas 614 enables the elimination of instability in the main stream.

(2-7) Drive Value Setting Step $S_7$

In this step $S_7$, the controller 9 sets the driving voltage supplied to the vibratory element 31 from the voltage supply unit 32 to the optimal drive value $V_s$ determined in the optimal drive value searching step $S_6$. With the optimal drive value $V_s$, it is possible to produce a main stream with no instability. Also, at the same time, charge inconsistencies among the droplets $D_2$ or the droplets $D_3$ are also eliminated in the side streams, making it possible to keep instability from occurring.

It is desirable to enable the side streams to enter straight into the space inside the collecting receptacle 82 or the collecting receptacle 83, such that droplets directly arrive at a liquid such as a cell culture solution inserted into the collecting receptacles 82 and 83 in advance. If there is instability occurring in the side streams, in some cases droplets entering the collecting receptacles 82 and 83 will collide into the inner walls of the receptacle, cells included in the droplets will be damaged, and the survival rate of collected cells will be lowered. In order to prevent the collision of droplets into the inner walls, it is effective to set the opening diameter of the collecting receptacles 82 and 83 to approximately 50% of the receptacle inner diameter or less, and adjust the positions of the side streams such that the side streams enter straight into the openings.

(2-8) Collecting Receptacle Returning Step $S_8$

When the above steps are completed and an optimal value $V_s$ is set such that the drive value V of the vibratory element 31 produces a stable main stream and side streams, the controller 9 completes the control steps for optimizing the fluid stream S, and starts cell analysis/sorting. At this point, the collecting receptacle 811 that was retracted from out between the deflecting plates 51 and 52 in step $S_1$ is returned to the initial position. For the initial position of the collecting receptacle 811, see FIG. 1.

As above, in the flow cytometer 1, the drive value V of the vibratory element 31 is automatically adjusted to produce a straight fluid stream S with no instability. For this reason, with the flow cytometer 1, manual fluid stream optimization, which were required every time the flow cell or microchip was replaced, or for every analysis in the past, are made unnecessary, enabling easy and high-precision analysis.

3. Second Procedure for Optimization Control of Fluid Stream in Microparticle Sorting Device According to Present Technology In the above control steps, there was described a first procedure that obtains, in the image acquiring/pixel information acquiring step $S_5$, a drive value $V_s$ for the vibratory element 31 that potentially optimizes a fluid stream S by image processing of an image acquired by the first camera 61. In a microparticle sorting device according to the present technology, it is possible to keep an optimized fluid stream S in a stable state by performing processing using an image acquired by the second camera 7, in conjunction with the processing using an image acquired by the first camera 61.

Figure 10:
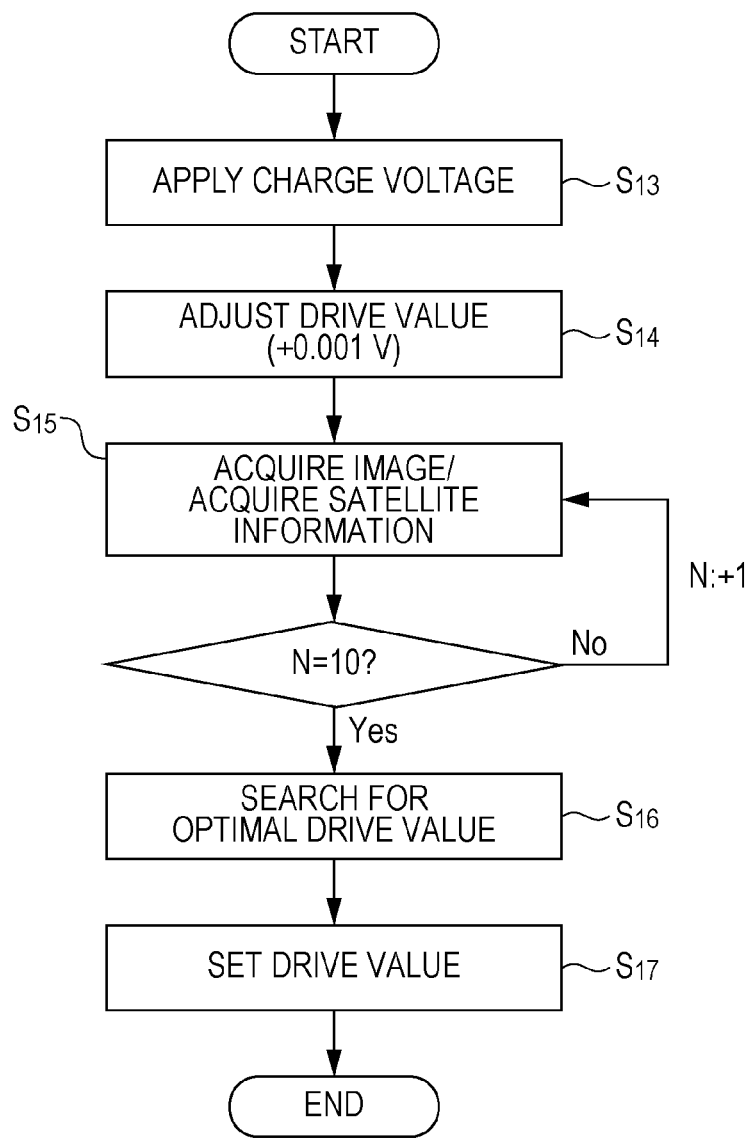
FIG. 10 is a flowchart for explaining an exemplary modification of control steps for optimizing a fluid stream S in the flow cytometer 1.

FIG. 10 is a flowchart for explaining a second procedure of control steps for optimizing a fluid stream S in the flow cytometer 1. The control steps include a "charge voltage applying step $S_{13}$", a "drive value adjusting step $S_{14}$", an "image acquiring/satellite information acquiring step $S_{15}$", an "optimal drive value searching step $S_{16}$", and a "drive value setting step $S_{17}$". Each step is described below.

(3-1) Charge Voltage Applying Step $S_{13}$

If an analysis start signal is input by a user, the controller 9 drives the pumps of tanks storing sample liquid and sheath liquid, and starts sending sample liquid and sheath liquid to the sample inlet 23 and the sheath inlet 24 of the microchip 2. Furthermore, the controller 9 starts the application of vibration to the orifice 21 by the vibratory element 31. Thus, a 3D laminar flow of sample liquid and sheath liquid projected from the orifice 21 is broken into droplets and ejected to produce a fluid stream S. At this point, the voltage supplied to the vibratory element 31 by the voltage supply unit 32 is taken to be the optimal value $V_s$ set in the first procedure discussed above. The fluid stream S is projected straight out from the orifice 21, and collected in the collecting receptacle 811 (see FIG. 1).

In this step $S_{13}$, the charge unit 41, having received a signal from the controller 9, starts charging droplets. Thus, droplets having a positive charge, droplets having no charge, and droplets having a negative charge come to be contained in the fluid stream S. Respective droplets are subjected to an electrical force acting between the deflecting plates 51 and 52, and travel in a direction according to their charge (see FIG. 2).

(3-2) Drive Value Adjusting Step $S_{14}$

In this step $S_{14}$, the controller 9 outputs a signal to the voltage supply unit 32, causing the driving voltage of the vibratory element 31 to increase or decrease from the optimal value $V_s$ by a fixed increment. The increment of change in the driving voltage in this step $S_{14}$ is preferably smaller than the increment of change in step $S_4$ of the first procedure discussed earlier (in the above example, 0.01 V).

(3-3) Image Acquiring/Satellite Information Acquiring Step $S_{15}$

Figure 11:
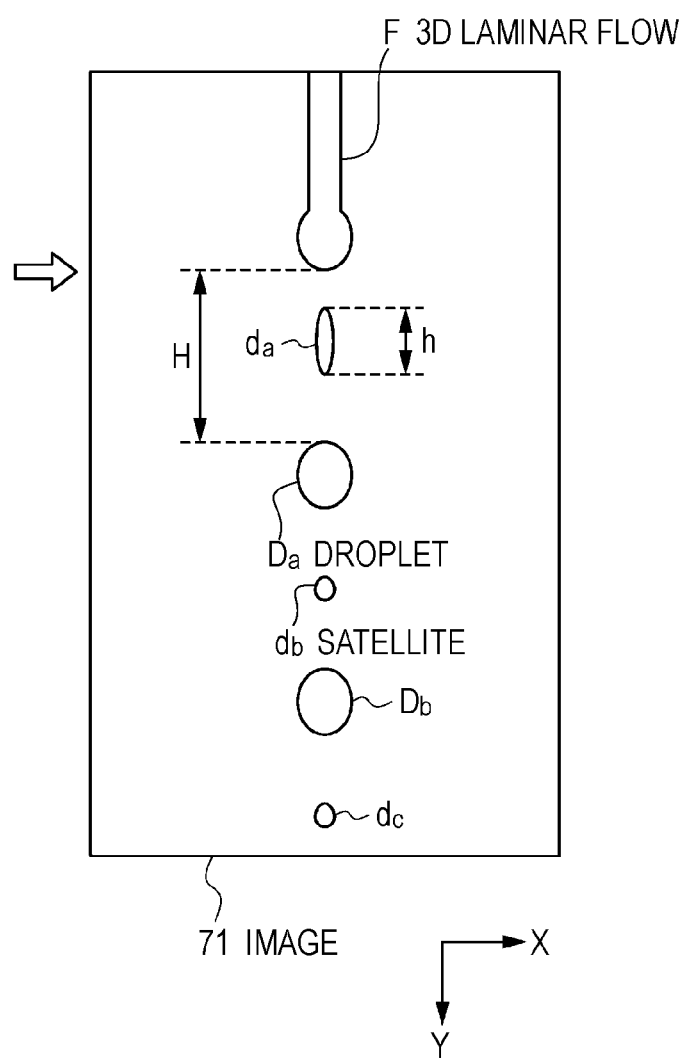
FIG. 11 is a diagram for explaining an image process in an image acquiring/satellite information acquiring step $S_5$.

If the drive value of the vibratory element 31 is set to $(V_s+0.001)$ V, for example, the controller 9 outputs a signal to the second camera 7, and the second camera 7 acquires an image of droplets in the fluid stream S. FIG. 11 illustrates an example of an acquired image.

In the image 71, the sign F indicates a 3D laminar flow exiting the orifice 21, while the signs $D_a$ and $D_b$ indicate droplets. The position at which the 3D laminar flow F breaks into droplets due to vibration applied to the orifice 21 from the vibratory element 31 (the break-off point) is indicated by a block arrow in the drawing. The sign H indicates the distance between the cell-containing droplet $D_a$ immediately after dividing off from the 3D laminar flow F (the last droplet) and the end of the 3D laminar flow F in the positive Y-axis direction. A droplet (satellite) $d_a$ is positioned between the last droplet $D_a$ and the 3D laminar flow F. The last droplet $D_a$ as well as the droplet $D_b$ illustrated in the drawing are droplets formed in synchronization with the frequency of the vibration applied to the orifice 21 from the vibratory element 31, and are droplets utilized in cell sorting. On the other hand, the satellites $d_a$, $d_b$, and $d_c$ illustrated in the drawing are droplets formed out of synchronization with the frequency of the vibratory element 31, and are droplets that do not contribute to analysis.

The inventors discovered that a fluid stream optimized according to the first procedure discussed earlier can be stabilized to a state with no instability in the case where the facing length h of the satellite $d_a$ along the travel direction (the Y-axis direction) is 30% to 70% of the distance H between the last droplet $D_a$ and the end of the 3D laminar flow F. In this step $S_{15}$, the distance H and the length h are detected by image recognition of the image 71, and the ratio therebetween (satellite information) is computed.

This step $S_{15}$ is repeatedly executed multiple times, in which the acquisition of an image 71 and the computation of the ratio between the distance H and the length h are performed for different values of the drive value V of the vibratory element 31. For example, in the case of increasing the drive value V of the vibratory element 31 by 0.001 V, at first image acquisition and ratio computation are performed after setting the drive value to $(V_s+0.001)$ V. Subsequently, image acquisition and ratio computation are performed up to an Nth time while taking the drive value to be $(V_s+0.001 \times N)$ V. The number of repetitions N may be set as appropriate, and may be approximately 10 times, for example.

(3-4) Optimal Drive Value Searching Step $S_{16}$

After repeating the image acquiring/satellite information acquiring step $S_{15}$ a prescribed number of times, the controller 9 determines a second optimal drive value $V_s'$ such that the ratio of the length h versus the distance H becomes 30% to 70%. Specifically, the ratio of the length h versus the distance H is compared among the respective images 71 acquired in the image acquiring/satellite information acquiring step $S_{15}$ from the 1st to Nth times. Then, the repetition in which the ratio becomes 30% to 70% is identified, and the drive value V for that case is obtained as the second optimal drive value $V_s'$.

(3-5) Drive Value Setting Step $S_{17}$

In this step $S_{17}$, the controller 9 sets the driving voltage supplied to the vibratory element 31 from the voltage supply unit 32 to the second optimal drive value $V_s'$ determined in the optimal drive value searching step $S_{16}$, and starts cell analysis/sorting. With the second optimal drive value $V_s'$, it is possible to stabilize and produce a main stream with no instability.

As above, with the flow cytometer 1 it is possible to optimize a fluid stream S with image processing of an image acquired by a second camera 7, in combination with image processing of an image acquired by a first camera 61. Thus, with the flow cytometer 1 it is possible to finely adjust the optimal drive value Vs set according to the first procedure, and enable the stable formation of a straight fluid stream S with no instability.

Note that depending on the value of the drive value $V_s$ set according to the first procedure, the length h of the satellite $d_a$ may become extremely short in some cases. In this case, if one attempts to adjust the drive value V and set the length h to a length in the above range in the second procedure, a fluid stream S that was optimized according to the first procedure may once again enter an unstable state. In this case, by adjusting the emission timing of the strobe that illuminates the imaging area of the second camera 7, an image capturing a satellite $d_a$ of suitable length is acquired as the image from the second camera 7, and presented to the user. The length h of a satellite $d_a$ can be lengthened by quickening the emission timing of the strobe, while the length h can be shortened by slowing the emission timing.

A microparticle sorting device according to the present technology may also take configurations like the following.

(1) A microparticle sorting device equipped with a voltage supply unit that supplies a driving voltage to a vibratory element that applies vibration to an orifice that produces a fluid stream, a charge unit that imparts charge to at least some droplets ejected from the orifice, deflecting plates, arranged opposing each other with the fluid stream S therebetween, that vary a travel direction of the droplets, a first image sensor that acquires an image of the droplets passing between the deflecting plates, and a controller that detects the droplets in the image, sets a standard band corresponding to a width of the droplets before imparting the charge, and controls the driving voltage of the voltage supply unit so as to further decrease a quantity of the droplets detected in areas within a designated number of pixels from the standard band from among the droplets after imparting the charge.

(2) The microparticle sorting device according to (1) above, wherein the controller detects the standard band in an image of the droplets before imparting the charge, and sets the standard band in an image of the droplets after imparting the charge.

(3) The microparticle sorting device according (1) or (2) above, including a light source that irradiates the droplets passing between the deflecting plates with a laser, wherein the controller detects the droplets by image recognition of bright spots in the image.

(4) The microparticle sorting device according to (3) above, wherein the controller controls the driving voltage so as to further decrease a number of pixels in the bright spots detected in areas within a designated number of pixels from the standard band in an image of the droplets after imparting the charge.

(5) The microparticle sorting device according to (4) above, wherein the controller controls the driving voltage so as to minimize the number of pixels.

(6) The microparticle sorting device according to any of (1) to (5) above, including a second image sensor that acquires an image of the droplets at a position where fluid exiting the orifice breaks into droplets, wherein the controller controls the driving voltage such that a facing length along a travel direction of a droplet positioned between a microparticle-containing droplet immediately after dividing off from the fluid and the fluid becomes a designated length in the image.

(7) The microparticle sorting device according to (6) above, wherein the designated length is 30% to 70% of a distance between the microparticle-containing droplet and the fluid.

(8) The microparticle sorting device according to any of (1) to (7) above, wherein the first image sensor captures the droplets passing between the deflecting plates from a direction orthogonal to the fluid stream as well as a direction of opposition between the deflecting plates.

(9) The microparticle sorting device according to (1) to (8) above, wherein the deflecting plates vary a travel direction of the droplets with an electrical force acting on the charge imparted to the droplets.

(10) The microparticle sorting device according to any of (1) to (9) above, wherein the orifice is formed on a replaceable microchip.

Also, a method of optimizing a fluid stream according to the present technology may also take configurations like the following.

(11) A method of optimizing a fluid stream in a microparticle sorting device, including a first image acquiring step that acquires an image of droplets in a fluid stream produced from an orifice to which vibration is applied by a vibratory element, after passing between deflecting plates that vary a travel direction of the droplets, and a first voltage controlling step that detects the droplets in the image, sets a standard band corresponding to a width of the droplets before imparting charge, and sets the driving voltage of the vibratory element so as to further decrease a quantity of the droplets detected in areas within a designated number of pixels from the standard band from among the droplets after imparting charge.

(12) The method of optimizing a fluid stream according to (11) above, wherein the first image acquiring step includes a step of acquiring an image of the droplets before imparting charge, and a step of acquiring an image of the droplets after imparting charge, and the first voltage controlling step includes a step of detecting the standard band in the image of the droplets before imparting charge, and a step of setting the standard band in the image of the droplets after imparting charge.

(13) The method of optimizing a fluid stream according to (11) or (12) above, wherein, in the first image acquiring step, the droplets passing between the deflecting plates are irradiated with a laser, and in the first voltage controlling step, the droplets are detected by image recognition of bright spots in the image.

(14) The method of optimizing a fluid stream according to (13) above, wherein, in the first voltage controlling step, the driving voltage is set so as to further decrease a number of pixels in the bright spots detected in areas within a designated number of pixels from the standard band in an image of the droplets after imparting the charge.

(15) The method of optimizing a fluid stream according to (14) above, wherein, in the first voltage controlling step, the driving voltage is controlled so as to minimize the number of pixels.

(16) The method of optimizing a fluid stream according to any of (11) to (15) above, including a second image acquiring step that acquires an image of the droplets at a position where fluid exiting the orifice breaks into droplets, and a second voltage controlling step that sets the driving voltage such that a facing length along a travel direction of a droplet positioned between a microparticle-containing droplet immediately after dividing off from the fluid and the fluid becomes a designated length in the image.

(17) The microparticle sorting device according to (16) above, wherein the designated length is 30% to 70% of a distance between the microparticle-containing droplet and the fluid.

(18) The method of optimizing a fluid stream according to (16) or (17) above, wherein the second image acquiring means and the second voltage controlling step are performed after the first image acquiring means and the first voltage controlling step.

(19) The method of optimizing a fluid stream according to any of (16) to (18) above, wherein the driving voltage is adjusted roughly in the first voltage controlling step, and the driving voltage is adjusted finely in the second voltage controlling step.

(20) The method of optimizing a fluid stream according to any of (11) to (19) above, wherein, in the first image acquiring step, the droplets passing between the deflecting plates are captured from a direction orthogonal to the fluid stream as well as a direction of opposition between the deflecting plates.

REFERENCE SIGNS LIST 1 microparticle sorting device
2 microchip
23 sample inlet
31 vibratory element
32 voltage supply unit
41 charge unit
42 electrode
51, 52 deflecting plate
61 first camera
610, 611, 71 image
612 standard line
613 standard band
614 correction target area
62 light source
7 second camera
81, 812, 82, 83 collecting receptacle
S fluid stream

The invention claimed is:
1. A microparticle sorting device comprising:
a voltage supply unit that supplies a driving voltage to a vibratory element that applies vibration to an orifice that produces a fluid stream;
a charge unit that imparts charge to at least some droplets ejected from the orifice;
deflecting plates, arranged opposing each other with the fluid stream therebetween, that vary a travel direction of the droplets;
a first image sensor that acquires an image of the droplets passing between the deflecting plates; and a controller that detects the droplets in the image, sets a standard band corresponding to a width of the droplets before imparting the charge, and controls the driving voltage of the voltage supply unit so as to further decrease a quantity of the droplets detected in areas within a designated number of pixels from the standard band from among the droplets after imparting the charge.

2. The microparticle sorting device according to claim 1, wherein
the controller detects the standard band in an image of the droplets before imparting the charge, and sets the standard band in an image of the droplets after imparting the charge.

3. The microparticle sorting device according to claim 2, comprising:
a light source that irradiates the droplets passing between the deflecting plates with a laser;
wherein the controller detects the droplets by image recognition of bright spots in the image.

4. The microparticle sorting device according to claim 3, wherein
the controller controls the driving voltage so as to further decrease a number of pixels in the bright spots detected in areas within a designated number of pixels from the standard band in an image of the droplets after imparting the charge.

5. The microparticle sorting device according to claim 4, wherein
the controller controls the driving voltage so as to minimize the number of pixels.

6. The microparticle sorting device according to claim 5, comprising:
a second image sensor that acquires an image of the droplets at a position where fluid exiting the orifice breaks into droplets;
wherein the controller controls the driving voltage such that a facing length along a travel direction of a droplet positioned between a microparticle-containing droplet immediately after dividing off from the fluid and the fluid becomes a designated length in the image.

7. The microparticle sorting device according to claim 6, wherein
the designated length is 30% to 70% of a distance between the microparticle-containing droplet and the fluid.

8. The microparticle sorting device according to claim 7, wherein
the first image sensor captures the droplets passing between the deflecting plates from a direction orthogonal to the fluid stream as well as a direction of opposition between the deflecting plates.

9. The microparticle sorting device according to claim 8, wherein
the deflecting plates vary a travel direction of the droplets with an electrical force acting on the charge imparted to the droplets.

10. The microparticle sorting device according to claim 9, wherein
the orifice is formed on a replaceable microchip.

11. A method of optimizing a fluid stream in a microparticle sorting device, comprising:
a first image acquiring step that acquires an image of droplets in a fluid stream produced from an orifice to which vibration is applied by a vibratory element, after passing between deflecting plates that vary a travel direction of the droplets; and
a first voltage controlling step that detects the droplets in the image, sets a standard band corresponding to a width of the droplets before imparting charge, and sets the driving voltage of the vibratory element so as to further decrease a quantity of the droplets detected in areas within a designated number of pixels from the standard band from among the droplets after imparting charge.

12. The method of optimizing a fluid stream according to claim 11, wherein
the first image acquiring step includes a step of acquiring an image of the droplets before imparting charge, and a step of acquiring an image of the droplets after imparting charge, and
the first voltage controlling step includes a step of detecting the standard band in the image of the droplets before imparting charge, and a step of setting the standard band in the image of the droplets after imparting charge.

13. The method of optimizing a fluid stream according to claim 12, wherein
in the first image acquiring step, the droplets passing between the deflecting plates are irradiated with a laser, and
in the first voltage controlling step, the droplets are detected by image recognition of bright spots in the image.

14. The method of optimizing a fluid stream according to claim 13, wherein
in the first voltage controlling step, the driving voltage is set so as to further decrease a number of pixels in the bright spots detected in areas within a designated number of pixels from the standard band in an image of the droplets after imparting the charge.

15. The method of optimizing a fluid stream according to claim 14, wherein
in the first voltage controlling step, the driving voltage is controlled so as to minimize the number of pixels.

16. The method of optimizing a fluid stream according to claim 15, comprising:
a second image acquiring step that acquires an image of the droplets at a position where fluid exiting the orifice breaks into droplets; and
a second voltage controlling step that sets the driving voltage such that a facing length along a travel direction of a droplet positioned between a microparticle-containing droplet immediately after dividing off from the fluid and the fluid becomes a designated length in the image.

17. The method of optimizing a fluid stream according to claim 16, wherein
the designated length is 30% to 70% of a distance between the microparticle-containing droplet and the fluid.

18. The method of optimizing a fluid stream according to claim 17, wherein
the second image acquiring means and the second voltage controlling step are performed after the first image acquiring means and the first voltage controlling step.

19. The method of optimizing a fluid stream according to claim 18, wherein
the driving voltage is adjusted roughly in the first voltage controlling step, and the driving voltage is adjusted finely in the second voltage controlling step.

20. The method of optimizing a fluid stream according to claim 19, wherein
in the first image acquiring step, the droplets passing between the deflecting plates are captured from a direction orthogonal to the fluid stream as well as a direction of opposition between the deflecting plates.

* * * * *